United States Patent
Moonen et al.

(10) Patent No.: US 10,252,979 B2
(45) Date of Patent: Apr. 9, 2019

(54) PROCESS FOR THE REDUCTIVE AMINATION AND SELECTIVE HYDROGENATION OF SUBSTRATES CONTAINING A SELECTED HALOGEN

(71) Applicant: Taminco BVBA, Ghent (BE)

(72) Inventors: Kristof Moonen, Hamme (BE); Bart Vandeputte, Hever (BE); Daan Scheldeman, Waregem (BE); Kim Dumoleijn, Eede (NL)

(73) Assignee: Taminco BVBA, Ghent (BE)

( * ) Notice: Subject to any disclaimer, the term of this patent is extended or adjusted under 35 U.S.C. 154(b) by 0 days.

(21) Appl. No.: 15/678,183

(22) Filed: Aug. 16, 2017

(65) Prior Publication Data

US 2017/0342019 A1 Nov. 30, 2017

Related U.S. Application Data

(62) Division of application No. 14/914,744, filed as application No. PCT/EP2014/068083 on Aug. 26, 2014.

(30) Foreign Application Priority Data

Sep. 4, 2013 (EP) .................................... 13183017

(51) Int. Cl.
*C07C 209/26* (2006.01)
*C07C 209/36* (2006.01)
*C07C 249/04* (2006.01)

(52) U.S. Cl.
CPC ........ *C07C 209/26* (2013.01); *C07C 209/365* (2013.01); *C07C 249/04* (2013.01)

(58) Field of Classification Search
CPC . C07C 209/26; C07C 249/04; C07C 209/365; C07C 211/29; C07C 211/52; C07C 251/48

See application file for complete search history.

(56) References Cited

U.S. PATENT DOCUMENTS

| | | | |
|---|---|---|---|
| 3,499,034 A | 3/1970 | Gonzalez | |
| 3,546,297 A | 12/1970 | Kosak | |
| 3,666,813 A | 5/1972 | Hindin et al. | |
| 3,830,756 A | 8/1974 | Sanchez et al. | |
| 4,024,274 A | 5/1977 | Druckrey et al. | |
| 5,011,996 A | 4/1991 | Kiel et al. | |
| 5,512,529 A | 4/1996 | Deller et al. | |
| 5,689,021 A | 11/1997 | Cordier et al. | |
| 6,410,806 B2 | 6/2002 | Oku et al. | |
| 6,429,335 B1 | 8/2002 | Kiel | |
| 6,462,236 B2 | 10/2002 | Liang et al. | |
| 7,230,134 B2 | 6/2007 | Borner et al. | |
| 2001/0056035 A1 | 12/2001 | Auer et al. | |
| 2007/0078282 A1 | 4/2007 | Schramm et al. | |
| 2010/0113778 A1 | 5/2010 | Wiegand et al. | |
| 2010/0274054 A1 | 10/2010 | Staeb et al. | |
| 2016/0002146 A1 | 1/2016 | Peters et al. | |
| 2016/0207874 A1 | 7/2016 | Moonen et al. | |

FOREIGN PATENT DOCUMENTS

| | | | |
|---|---|---|---|
| EP | 0 312 253 A2 | | 4/1989 |
| EP | 1 195 192 A1 | | 4/2002 |
| EP | 2 301 660 A1 | | 3/2011 |
| EP | 13173233.1 | * | 6/2013 |
| EP | 2 774 911 A1 | | 9/2014 |
| GB | 2 024 643 A | | 1/1980 |
| WO | WO 2013/017611 A1 | | 2/2013 |
| WO | WO 2014/135508 A1 | | 9/2014 |
| WO | WO2014/202436 | * | 12/2014 |
| WO | WO 2014/202436 A1 | | 12/2014 |
| WO | WO 2014/202441 A1 | | 12/2014 |
| WO | WO 2015/032653 A1 | | 3/2015 |

(Continued)

OTHER PUBLICATIONS

Cheng et al., "The effect of water on the hydrogenation of o-chloronitrobenzene in ethanol, n-heptane and compressed carbon dioxide", Applied Catalysis A: General 455, (2013), pp. 8-15.

Dan-Qian et al, "Hydrogenation of ionic liquids: An alternative methodology toward highly selective catalysis of halonitrobenzenes to corresponding haloanilines", Journal of Molecular Catalysis A: Chemical, 235, (2005), pp. 137-142.

Kratky et al, "Effect of catalyst and substituents on the hydrogenation of chloronitrobenzenes", Applied Catalysis A: General, 235, (2002), pp. 225-231.

Wang et al., "A green synthesis route of ortho-chloroaniline: Solvent-free selective hydrogenation of ortho-chloronitrobenzene over Pt-Ru/$Fe_3O_4$/C catalyst", Catalysis Communications, vol. 19, (2012), pp. 110-114.

(Continued)

*Primary Examiner* — Yevgeny Valenrod
*Assistant Examiner* — Blaine G Doletski
(74) *Attorney, Agent, or Firm* — Dennis V. Carmen

(57) ABSTRACT

Disclosed is a process for performing a chemical reaction selected from reductive amination and hydrogenation of a first functional group in an organic feed substrate, which feed substrate comprises at least one further functional group containing a halogen atom, wherein the halogen atom is selected from the list consisting of chlorine, bromine, iodine, and combinations thereof, in the presence of hydrogen and a heterogeneous catalyst comprising at least one metal from the list of Pd, Rh, and Ru, together with at least a second metal from the list consisting of Ag, Ni, Co, Sn, Cu and Au. The process is preferably applied for the reductive amination of 2-chloro-benzaldehyde to form 2-chloro-benzyldimethylamine, as an intermediate in the production of agrochemically active compounds and microbiocides of the methoximinophenylglyoxylic ester series. Further disclosed is a composition rich in 2-chloro-benzyldimethylamine, further comprising an amount of 2-chloro-benzyl alcohol and being low in chlorotoluene isomers.

11 Claims, No Drawings

(56) References Cited

FOREIGN PATENT DOCUMENTS

WO    WO 2016/071410 A1    5/2016

OTHER PUBLICATIONS

Mahata et al., "Promotional effect of Cu on the structure and chloronitrobenzene hydrogenation performance of carbon nanotube and activated carbon supported Pt catalysts", Applied Catalysis A: General 464-465, (2013), pp. 28-34.
Han et al., "Effect of transition metal (Cr, Mn, Fe, Co, Ni and Cu) on the hydrogenation properties of chloronitrobenzene over Pt/TiO$_2$ catalysts", Journal of Molecular Catalysis A: Chemical, 209, (2004), pp. 83-87.
Coq et al.:"Influence of alloying platinum for the hydrogenation of p-chloronitrobenzene over PtM/Al$_2$O$_3$ catalysts with M=Sn, Pb, Ge, Al, Zn", Journal of Molecular Catalysis, vol. 71, Issue 3, Feb. 1, 1992, pp. 317-333.
Tijani et al., "Hydrogenation of para-chloronitrobenzene over supported ruthenium-based catalysts", Applied Catalysis, vol. 76, issue 2, Sep. 16, 1991, pp. 255-266.
Cárdenas-Lizana et al., "Pd-promoted selective gas phase hydrogenation of p-chloronitrobenzene over alumina supported Au", Journal of Catalysis, vol. 262, (2009), pp. 235-243.
Bhattacharyya, "A high throughput synthesis of N,N-dimethyl tertiary amines", Synthetic Communications, vol. 30, No. 11, (2000), pp. 2001-2008.
PCT International Search Report and Written Opinion of the International Searching Authority dated Dec. 17, 2014 for International Application No. PCT/EP2014/068083 12 pages.
PCT Second Written Opinion of the International Preliminary Examining Authority dated Sep. 8, 2015 for International Application No. PCT/EP2014/068083 7 pages.
European Patent Application No. 13173233.1 filed Jun. 21, 2013; Applicant: BASF SE (Machine Translation) 32 pages.
European Patent Application No. 14151747.4 filed Jan. 20, 2014; Applicant: BASF SE (Machine Translation) 33 pages.
Co-pending U.S. Appl. No. 15/344,846, filed Nov. 7, 2016; Moonen et al. Specification 49 pages, Claims 4 pages, Abstract 1 page.
Bagal et al.; "PS-Pd-NHC: an efficient and heterogeneous recyclable catalyst for direct reductive amination of carbonyl compounds with primary / secondary amines in aqueous medium"; Catalysis Science & Technology; 2012; 2; pp. 354-358.
Drinkel et al.; "Zwitterionic-Surfactant-Stabilized Palladium Nanoparticles as Catalysts in the Hydrogen Transfer Reductive Amination of Benzaldehydes" The Journal or Organic Chemistry; 2014; 79; pp. 2574-2579.
Wang et al.; "Single-phase bimetallic system for the selective oxidation of glycerol to glycerate"; Chem. Commun. (The Royal Society of Chemistry); 2006; pp. 1956-1958.
Enache et al.; "Solvent-Free Oxidation of Primary Alcohols to Aldehydes Using Au-Pd/TiO$_2$ Catalysts"; Science; 2006; vol. 311; pp. 362-365.
PCT International Search Report and Written Opinion of the International Searching Authority dated Apr. 26, 2017 for International Application No. PCT/IB2016/001904 15 pages.
PCT International Search Report and Written Opinion of the International Searching Authority dated Jan. 25, 2016 for International Application No. PCT/EP2015/075734 11 pages.
Co-pending U.S. Appl. No. 15/523,864, filed May 2, 2017; Moonen et al. specification 33 pages, Claims 4 pages, Abstract 1 page.
Notice of Allowance dated Aug. 16, 2018 received in co-pending U.S. Appl. No. 14/914,744 12 pages.
Co-pending U.S. Appl. No. 14/914,744, filed Feb. 26, 2016; Moonen et al. Claims 4 pages, Specification 38 pages, Abstract 1 page.
Office Action dated Dec. 13, 2016 received in co-pending U.S. Appl. No. 14/914,744 35 pages.
Notice of Allowance dated Aug. 10, 2017 received in co-pending U.S. Appl. No. 14/914,744 15 pages.
Office Action dated Feb. 7, 2018 received in co-pending U.S. Appl. No. 14/914,744 45 pages.
Office Action dated Apr. 6, 2018 received in co-pending U.S. Appl. No. 15/523,864 9 pages.
Office Action dated Jul. 9, 2018 received in co-pending U.S. Appl. No. 15/344,846 12 pages.
Notice of Allowance dated Oct. 16, 2018 received in co-pending U.S. Appl. No. 15/523,864 8 pages \* cited by examiner

PROCESS FOR THE REDUCTIVE AMINATION AND SELECTIVE HYDROGENATION OF SUBSTRATES CONTAINING A SELECTED HALOGEN

This application is a divisional application of and claims priority to U.S. application Ser. No. 14/914,744, filed on Feb. 26, 2016, which is the national stage filing under 35 U.S.C. § 371 of PCT/EP2014/068083, filed Aug. 26, 2014, which claims priority to European Application EP 13183017.6, filed Sep. 4, 2013, the contents of which are incorporated herein by reference in their entirety.

FIELD OF THE INVENTION

The present invention relates to chemical reactions which involve the chemical conversion of a first functional group in an organic feed substrate, in the presence of hydrogen, whereby the organic feed substrate comprises at least one further functional group containing a halogen atom other than fluorine. More particularly, the invention relates to the noble metal catalysed reactions selected from the reductive amination and the selective hydrogenation of only the first functional group on the substrate while keeping the further functional group containing the halogen atom substantially untouched and present in the reaction product.

BACKGROUND OF THE INVENTION

The selective conversion of one functional group in a multifunctional feed substrate has been an area of continuous high interest throughout the chemical, pharmaceutical and agrochemical industry. In particular, halogen atoms are often incorporated next to other functional groups in active ingredients or in precursors of those active ingredients.

The objective of high selectivity has often been rather elusive, because most processes are prone to side reactions leading to significant amounts of byproducts. These side reactions are consuming valuable amounts of feed substrate, and the byproducts are often rather useless. Some of the byproducts may also be difficult to separate from the desired product. In cases where the desired product is an intermediate for the production of a further derivative, some of the byproducts may also be disturbing for further synthesis steps because they may be reactive in such downstream process step and may lead to undesired additional consumption of valuable raw materials and even to undesirable and/or unacceptable end product contamination.

Multi-step synthesis protocols of complex multifunctional chemicals more and more comprise catalytic conversion steps as these often outperform their stoichiometric alternatives with respect to atom efficiency and reduced waste generation. Reductive conversion steps with hydrogen gas as the reducing agent typically use metal based catalysts in order to proceed at rates of commercial interests.

Metals, however, often interfere with carbon-halogen bonds in organic compounds. Pd in particular is for instance capable of inserting into a carbon-halogen bond. Such behaviour is desired in its use as catalyst in so-called coupling reactions. Such reactions are often used as key steps in multi-step synthesis paths for complex organic compounds, such as active ingredients in pharmaceutical or agrochemical industry. In a coupling reaction, a halogen containing first fragment is coupled with a second fragment by means of a catalyst, in which the second fragment is coupled to the first fragment at the position where the halogen was originally located. The second fragment may be coupled via a large variety of functional groups, and different versions of such coupling reactions have often received specific names, such as the Heck coupling, which is using an olefin, the Sonogashira coupling, which is using an alkyne, the Suzuki coupling, which is using a boronic acid and the Stille coupling, which uses an alkyl tin group. This list is far from exhaustive, because many more different functional groups may possibly be used for such coupling.

Insertion of a metal such as Pd into a carbon-halogen bond in the presence of hydrogen but in the absence of a suitable fragment to couple usually results in the displacement of the halogen atom by a hydrogen atom and hence the loss of the halogen (X) as part of the substrate. Such hydrogenolysis reaction is especially enhanced in the presence of a base which may capture the liberated acid HX. This reaction may be used advantageously in some applications, such as environmental treatment of halogenated organic pollutants.

For the production of the halogenated fragments to be used in subsequent coupling reactions, or in case halogen atoms are required in the structure of the final product, the insertion of the metal catalyst into the carbon-halogen bond is not desired, as it usually leads to side reactions and associated material losses. Not all halogens are evenly sensitive for this dehalogenation side reaction. The risk for dehalogenation is particularly high with chlorine, bromine and iodine, and much lower with fluorine-containing substrates.

A variety of methods have therefore been attempted in order to increase the selectivity of metal catalyzed reductive aminations and selective hydrogenations of one functional group in the presence of one or more halogen atoms elsewhere in the substrate molecule, in particular for chlorine, bromine and iodine. The methods which are currently available in the prior art may be subdivided into three classes.

A first method involves the addition of modifiers to the reaction mixture or working into alternative reaction media. U.S. Pat. No. 6,429,335 B1 for instance discloses a process for the reductive amination of ortho-chlorobenzaldehyde with ammonia under 140 bar of hydrogen using Raney nickel or Raney cobalt to produce the primary amines ortho-chlorobenzylamine. The process operates in the presence of an amount of disodium tetraborate decahydrate (borax), optionally together with a small amount of bis (hydroxyethyl) sulphide, and obtains a product selectivity of at most 95.87% wt. The main byproduct is 3.19% wt of ortho-chlorobenzyl alcohol, and only 0.1% wt of benzylamine was found.

Cheng et al., in "The effect of water on the hydrogenation of o-chloronitrobenzene in ethanol, n-heptane and compressed $CO_2$", Applied Catalysis A: General 455 (2013), pp. 8-15, Elsevier, discloses the effect of water or the use of compressed carbon dioxide as the reaction medium on the hydrogenation of o-chloronitrobenzene to o-chloro aniline over 5% Pd or Pt on a carbon support as the catalyst. The reaction is performed at 35° C. and under a hydrogen pressure of 40 bar. The Pd catalysts however suffer of poor stability under these conditions.

Dan-Qian Xu et al, "Hydrogenation of ionic liquids: An alternative methodology toward highly selective catalysis of halonitrobenzenes to corresponding haloanilines", Journal of Molecular Catalysis A: Chemical, 235 (2005), pp. 137-142, Elsevier, addresses the same reaction. The process uses Raney nickel, 5% Pt/C and 5% Pd/C catalysts in different ionic liquids, with methanol as the reference solvent. Markedly lower dehalogenation was observed with the ionic liquid catalyst systems as compared to the methanol reference. The drawback of the use of special reaction media or the addition of modifiers is the extra complexity which needs to be built into the process.

A second method involves modifying the catalyst support in order to improve the selectivity. US 2007/0078282 A1 performs in its Example 4 the reductive amination of F-benzaldehyde with a monometallic catalyst of nickel on carbon (Kataleuna 6504 K). Kratky V. et al, "Effect of catalyst and substituents on the hydrogenation of chloronitrobenzenes", Applied Catalysis, A: General, 235 (2002), pp. 225-231, Elsevier, discloses a process for the liquid phase hydrogenation of chloronitrobenzene isomers to the corresponding chloroanilines. The process uses either a palladium on charcoal catalyst (Pd/C) or a palladium on sulphonated poly(styrene-co-divinylbenzene) catalyst (Pd/D). Only the Pd/D catalyst was activated, i.e. reduced prior to its use in the reaction. The highest selectivity obtained towards the desired end-product was lower than 95%. Significant dechlorination was observed, primarily of the feed substrate over the Pd/C catalyst, and of the reaction product over the Pd/D catalyst.

A third method involves modifying the parent hydrogenation catalysts with additional metals, so-called promoters. Wang, Y. et al., "A green synthesis route of ortho-chloroaniline: solvent-free selective hydrogenation of ortho-chloronitrobenzene over Pt—Ru/Fe$_3$O$_4$/C catalyst", Catalysis Communications 19 (2012) 110-114, Elsevier, discloses the use of Pt—Ru/Fe$_3$O$_4$/C catalyst for the selective hydrogenation of o-chloro nitrobenzene at temperatures between 75 and 85° C. and a pressure between 17 and 40 bar. High conversion is reported with virtually no dehalogenation. U.S. Pat. No. 3,666,813 reports the use of Bi, Pb and Ag modified Pt/C catalysts and a Pb modified Pd/C catalyst for the hydrogenation of chlorinated nitrobenzenes at temperatures between 75 and 100° C. and a pressure of 750 psig. While the parent Pd and Pt catalyst showed complete (100%) dehalogenation under these conditions, the modified catalysts showed a reduced dehalogenation down to levels below 5%. Mahata, N. et al., "Promotional effect of Cu on the structure and chloronitrobenzene hydrogenation performance of carbon nanotube and activated carbon supported Pt catalysts", Applied catalysis A: General 464-465 (2013) 28-34, Elsevier, shows that the presence of Cu as a promoter in a Pt catalyst with carbon nanotubes or activated carbon as the support results in the reduction of the level of dehalogenation and an increase of the catalyst stability in the hydrogenation of chloronitrobenzene at 120° C. and 15 bar. U.S. Pat. No. 5,512,529 discloses the use of a platinum catalyst on an active carbon support and modified by copper in the hydrogenation of halonitro compounds to aromatic haloamines.

Pt based catalysts are frequently contemplated in case of sensitive hydrogenation reactions. Examples of Pt-based multimetallic catalysts may be found in GB 2024643, U.S. Pat. No. 3,546,297, EP 2301660 A1, and also in the articles by Han et al.: "Effect of transition metal (Cr, Mn, Fe, Co, Ni and Cu) on the hydrogenation properties of chloronitrobenzene over Pt/NiO2 catalysts", Journal of Molecular Catalysis A: Chemical, vol. 209, No, 1-2, 1 Feb. 2004, pages 83-87, or by Coq et al.: "Influence of alloying platinum for the hydrogenation of chloronitrobenzene over PtM/Al2O3 catalysts with M=Sn, Pb, Ge, Al, Zn", Journal of Molecular Catalysis, vol. 71, 1 Jan. 1992, pages 317-333. U.S. Pat. No. 3,499,034 discloses Pd—Pt catalysts which have been promoted with iron, Fe. US 2001/0056035 A1 discloses a series of multimetallic catalysts which are all based on iridium, Ir, doped with one or more additional metals. In a comparative example, US 2001/0056035 A1 uses a bimetallic catalyst with platinum in combination with copper, Cu. However, these catalysts are very costly because of the scarcity of the platinum or of the other precious metals involved.

U.S. Pat. No. 5,689,021 discloses the use of a Raney Nickel catalyst, prepared from the nickel-rich crystalline precursor Ni$_2$Al$_3$, and doped with the addition element molybdenum to obtain Ni$_{2-x}$/Al$_3$/Mo$_x$, with x=0.4±0.05, in order to selectively hydrogenate various halonitroaromatics to form the corresponding haloaminoaromatics. The hydrodehalogenation side reaction was found to be virtually nonexistent.

Other chemical pathways to obtain particularly valuable polyfunctional products containing halogens have also been explored.

The stoichiometric alternative to the catalytic reductive amination of o-chloro benzaldehyde to obtain o-chloro benzyldimethylamine is exemplified by WO 2013/017611 A1, which describes a process to obtain o-chloro-benzyldimethyl amine from o-chlorobenzyl chloride and dimethylamine. The yield of the reaction was at most 95.4% of theory. The reaction was performed without involving any catalyst and a chloride salt was obtained as an undesired byproduct. Such processes based on stoichiometric chemistry in general suffer from poor atom efficiency and production of large amounts of waste.

There therefore remains a need for a highly selective conversion in chemical reactions selected from the reductive amination and the selective hydrogenation of only the first functional group, on a substrate containing at least one further functional group containing a halogen atom. The desire is to achieve industrially acceptable reaction rates while keeping the further functional group containing the halogen atom substantially untouched and present in the reaction product.

It is an objective of the process according to the present invention to carry out the selected chemical reaction with a low degree of dehalogenation. Fluorine is known to be significantly less sensitive to dehalogenation than the heavier and more bulky halogens chlorine, bromine and/or iodine: a fluorine atom initially present in the feed substrate molecule therefore has a higher likelihood to remain present in the reaction product as compared to the other halogens. There therefore remains a particular need for a highly selective catalyst which will allow a low degree of dehalogenation in a substrate containing at least one further functional group containing chlorine, bromine and/or iodine.

The present invention aims to obviate or at least mitigate the above described problem and/or to provide improvements generally.

SUMMARY OF THE INVENTION

According to the invention, there is provided a process and a particularly useful composition which may be prepared using the process, as defined in any of the accompanying claims.

The invention therefore provides a process for performing a chemical reaction selected from the reductive amination and the selective hydrogenation of a first functional group in an organic feed substrate, which feed substrate comprises at least one further functional group containing a halogen atom, wherein the halogen atom is selected from the list consisting of chlorine, bromine, iodine, and combinations thereof, in the presence of hydrogen and a heterogeneous catalyst comprising at least one first metal selected from the list consisting of palladium, Pd, rhodium, Rh, and ruthenium, Ru, together with at least one second metal selected from the list consisting of silver, Ag, nickel, Ni, cobalt, Co, tin, Sn, copper, Cu, and gold, Au.

The applicants select the first metal from the list consisting of palladium, Pd, rhodium, Rh, and ruthenium, Ru. More preferably the applicants use palladium as the first metal. Palladium is more readily available than most of the other noble metals in the list of first metals, and is therefore more readily obtainable as a raw material, usually also at a lower cost for the production of the catalyst. Palladium is also a metal which is easier to recover or to recuperate from a spent catalyst, and to recycle into a new use. Even more preferably, the applicants use a bimetallic catalyst with Pd being selected as the first metal and only one metal being selected as the second metal. A bimetallic catalyst is easier to produce and its quality may be more readily controlled. Yet more preferably the applicants use a bimetallic Pd/Cu catalyst, i.e. with only copper as the second metal. The applicants have found that copper is also very readily available in a suitable form for the catalyst manufacture, and also that copper readily outperforms the other metals of the second list in at least some of the selected chemical reactions according to the present invention.

Although palladium is not recognized as a highly selective catalyst for performing reductive aminations and hydrogenation reactions of substrates containing halogens, we have found that the catalysts containing palladium as the first metal, such as Pd—Cu bimetallic catalysts, surprisingly combine the benefits of the high activity of the Pd catalysts with a greatly improved selectivity when reacting halogen containing substrates. The applicants believe that this advantage may also be present with a selected number of other first metals, as specified, and in combination with a number of second metals, as also specified.

We have found that the process according to the present invention is highly selective in performing the desired chemical conversion of the first functional group, while keeping the further functional group containing the halogen atom substantially intact such that the halogen remains present in the reaction product. We have for instance found that the dehalogenation of a halide function as the further functional group on the substrate, a side reaction which is occurring when using monometallic palladium catalyst, may be significantly suppressed, and essentially avoided, when using the process according to the present invention. The dehalogenated byproduct is typically useless, and possibly even a nuisance. The same may apply to the halide containing byproduct (e.g. HX) of the undesired dehalogenation reaction, which for instance may cause corrosion to the reactor or downstream processing equipment. The side reaction thus typically represents a downgrade of valuable starting materials, and adds additional burden for removal of the byproducts from the desired reaction product or for selecting more precious construction materials. The process according to the present invention thus brings the advantage of producing a highly pure desired reaction product, which requires much less clean-up, if any, before it may be put to further use. The process also brings the advantage of highly efficient use of the starting organic substrate, with very low downgrade, if any, to byproducts which may be useless or undesired in the prime reaction product, in which case the byproducts must be separated off and typically discarded or even require additional efforts for disposal in a responsible manner. Furthermore the process according to the present invention avoids the use of expensive and generally less active platinum as the metal in the catalyst without compromising the selectivity.

The applicants have found that the process according to the present invention may be particularly suitable for the reductive amination of ortho-chloro-benzaldehyde in the presence of dimethyl amine, DMA, to produce ortho-chloro benzyl dimethyl amine, o-Cl-BDMA. The applicants have found that the process according to the present invention may produce the desired o-Cl-BDMA, also known as ortho-Cl-BDMA or 2-Cl-BDMA, in very high yield and in particularly high purity, with very little byproducts.

The invention therefore also provides a composition comprising, as measured by gas chromatography, GC,
a) at least 98.0% wt of o-chloro-benzyl-dimethylamine, o-Cl-BDMA,
b) at most 0.40% wt of ortho-chloro toluene, preferably the total of all chloro toluene isomers, and
c) at least 0.05% wt of o-chloro-benzyl alcohol.

The applicants have found that this composition is particularly suitable as an intermediate for the production of more complex structures in multi-step synthesis routes. Such routes may lead to agrochemical or pharmaceutical active ingredients. The applicants believe that the low presence in the composition of ortho-chloro toluene, more generally the total of all chloro toluenes, in particular of the mono chloro toluenes, and preferably also of chloro dichloromethyl benzenes, also known as chloro benzalchlorides, in particular of o-chloro dichloromethyl benzene, also known as 2-chloro benzyl dichloride or ortho-chloro benzalchloride, preferably below the detection limit in the most appropriate analytical technique, and more preferably the total absence thereof, makes the composition highly suitable for use as raw material in the further steps of many synthesis routes. The applicants have found that the compounds such as a chloro toluene, such as mono chloro toluene, and ortho-chloro dichloromethyl benzene, are contaminants which participate in downstream steps when the composition is used as an intermediate for the synthesis of complex chemical compounds. However, they do not lead to the desired compound and hence represent a loss of valuable reagents. The compounds which result from these contaminants are at best inert but may also exhibit effects which are undesired in the final composition, in which case an excessive occurrence of these side reactions creates a need for extra purification steps in the overall synthesis process.

The composition is in particular useful if such further steps comprise metallation reactions such as lithiation or Grignard reactions, such as described in US 2010/0113778 A1, or coupling reactions such as the reactions known as the Heck, the Sonogashira, the Suzuki or the Stille coupling.

The applicants have found that a small amount of o-chloro-benzyl alcohol being present in the composition according to the present invention, which may for instance be present when the composition is obtained using the process according to the present invention, is of little consequence for the further use of the composition, such as in many further synthesis steps and/or many uses of the products thereof.

DETAILED DESCRIPTION

The present invention will be described in the following with respect to particular embodiments and with reference to certain drawings but the invention is not limited thereto but only by the claims. Any drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B. Accordingly, the terms "comprising" and "including" encompass the more restrictive terms "consisting essentially of" and "consisting of".

The terms "ortho", "meta" and "para", abbreviated by o-, m-, p- respectively, are used to indicate the relative position of two substituents on an aromatic cycle, as defined by the International Union of Pure and Applied Chemistry (IUPAC). Taking the standard priority rules for functional groups and substituents into account, their positioning may also be referred to by numbers in chemical nomenclature. In this respect, the indication 2-, 3-, and 4-correspond to o-, m-, and p- respectively.

In an embodiment, the current invention involves the use of a Pd—Cu catalyst for the reductive conversion of halogenated substrates in the presence of hydrogen, and in particular the reductive amination of such substrates. Being a catalytically very active metal, Pd has the advantage over Pt of being much cheaper and easier to recover.

Pd—Cu bimetallic catalysts have already found an application in environmental chemistry for nitrate reduction with hydrogen in waste water treatment, where biological denitrification is no longer appropriate.

Also described in the art is the effect of the hydrogen reduction on the structure of silica supported Pd—Cu bimetallic catalyst. A method for preparation of such a catalyst involving consecutive deposition of Pd and Cu on a silica support has been described, but no application of the catalyst was demonstrated.

Pd—Cu bimetallic catalysts have so far found limited applications in the manufacture of organic chemicals.

One reference describes the use of unsupported Pd—Ni, Pd—Cu and Pd—Ag catalysts for the hydrogenation of nitrobenzene to aniline. An improved activity was observed as compared to a palladium black reference. The highest activity was observed for the Pd—Ni catalyst. The introduction of a second metal was believed to lead to a better dispersion of the active centres on the catalyst surface.

Another reference describes the preparation of an active carbon supported Pd—Cu catalyst. Its use is demonstrated in the hydrogenation of acid halides to the corresponding aldehydes and in the stereospecific reduction of 6-deoxy-6-demethyl-6-methylene-5-oxytetracycline.

Yet another reference reports that the alloying of copper with palladium deposited on carbon in the respective weight ratio of less than 0.5:1.0 substantially enhances the catalytic activity of that palladium as a catalyst in the reduction of formyl benzoic acid impurities in crude phthalic acid.

Yet another reference describes the preparation and use of Pd—Cu and Pt—Cu bimetallic catalysts, optionally supported on a carrier, for the hydrogenation in the gas phase of succinic or maleic acid or their anhydrides to gamma-butyrolactone. The catalysts have the advantage of being able to hydrogenate both the carbonyl group and the site of the ethylenic unsaturation in a single step.

Yet another reference reports the use of Pd—Cu bimetallic nanoparticles as a catalyst for the reduction of p-nitrophenol to p-aminophenol using $NaBH_4$.

EP 0312253 A2 discloses a process for preparing tridodecylamine through an amination reaction of dodecyl alcohol with ammonia using Cu/Ni and Cu/Ni/Pd catalysts. It is shown that the presence of palladium reduces the reaction time and enhances the yield of tridodecylamine.

In none of these references disclosing a Pd—Cu multimetallic catalyst, the effect of such catalyst on halogenated substrates, in particular in maintaining the halogen atom in the structure of the final product, has been suggested or demonstrated.

The process according to the present invention is performed in the presence of hydrogen. The use of hydrogen ($H_2$) as the reducing agent is much favoured by the presence of a metal catalyst. Such a catalyst believed to be instrumental in activating the molecular hydrogen by weakening the H—H bond. This functionality is not particular for, or limited to reductive aminations, but is similar for all kind of hydrogenation reactions in organic chemistry. Next to the activation of $H_2$, the catalyst may also play a role in other reaction steps, such as the other steps involved in the reductive amination mechanism. This role together with the characteristics of the reaction conditions (such as the presence of free amine, water, the typical temperature and pressure range, etc. . . . ) make that reductive amination catalysts are often tailored for this specific process, especially when sensitive (e.g. multifunctional) substrates are involved. It was therefore surprising to see that the Pd—Cu catalyst of this invention was found to show such good halogen retention properties for a wide array of hydrogenation reactions of halogenated substrates, and that it is thus also applicable in a much broader technical field than only in reductive aminations.

Suitable organic feed substrates for the process according to the current invention are organic molecules containing at least one reducible functional group next to at least one halogen atom.

In an embodiment of the process according to the present invention, the first functional group is selected from the list consisting of an aldehyde, a ketone, a nitro group, a carboxylic acid, a carboxylic ester, a carboxylic amide, an unsaturated carbon-carbon bond, a nitrile, an imine and an oxime, and combinations thereof. Reducible functional groups which may suitably be hydrogenated with the Pd/Cu catalyst according to the process of the present invention are ketones, aldehydes, nitro groups, carboxylic acids, carboxylic esters, carboxylic amides, unsaturated carbon-carbon bonds, nitrile, imine and oxime groups. Such functional groups may be present in the substrate already when this is entered into the reactor, but may also be generated in situ during the course of a chemical reaction.

In an embodiment of the process according to the present invention, the first functional group in the feed substrate is first converted in situ by reaction with an additional reagent to form a reducible functional group. In particular, ketones and aldehydes may be converted to various intermediates, under the conditions of a reductive amination reaction, and which intermediates are subsequently hydrogenated with hydrogen to the final product of the reaction.

The halogen atom (X) is an element from group 17 in the IUPAC periodic table dated 22 Jun. 2007. In the process according to the present invention, the halogen atom is selected from the list consisting of chlorine, bromine or iodine, and combinations thereof, preferably the further functional group being selected from the list consisting of a chloride, a bromide and an iodide. The halogen is typically attached to the substrate by means of a covalent bond with a carbon atom (C—X bond). The carbon atom to which the halogen is attached may be either sp, $sp^2$ or $sp^3$ hybridized.

In an embodiment, the process according to the present invention is for the reductive amination of a halo-benzaldehyde in the presence of a nitrogen containing compound, preferably the nitrogen compound being selected from ammonia, a primary amine and a secondary amine, and mixtures thereof, preferably for the production of ortho-chloro benzyl dimethyl amine, o-Cl-BDMA, by the reductive amination of ortho-chloro-benzaldehyde in the presence of dimethyl amine, DMA.

For a reductive amination, chloro benzaldehydes (ortho, meta or para) are particular interesting substrates, as they may lead to the corresponding chloro benzylamines. Both the chloro and the amine functionality in these reaction products make the products of interest as further chemical building blocks, because the functionalities represent suitable points for further functionalization in subsequent synthesis steps. The chlorine atom offers opportunities for metallation reactions, such as lithiation or Grignard reactions, while the amine group offers possibilities for a further reductive amination or in case of a tertiary amine for quaternisation and conversion into other suitable leaving groups.

Reductive amination is the reaction well known in chemistry for the synthesis of primary, secondary or tertiary amines starting from a suitable ketone or aldehyde. The term "amination" relates to the reaction part in which an amine functionality is incorporated into the substrate. The term "reductive" relates to the observation, when comparing the feed substrate and the product of a reductive amination reaction, that a reduction has necessarily also taken place. In chemistry, a reduction reaction refers in general to the gain of electrons of an atom or a molecule. In organic chemistry, reductions are usually related with the disappearance of unsaturations, such as double bonds, from the substrate molecules. The net result of a reductive amination of a ketone or aldehyde is the conversion of a C=O double bond into a C—N single bond.

In an embodiment of the process according to the present invention, the reductive amination is performed in two steps, in the first step reacting the aldehyde with the nitrogen containing compound, and in the subsequent step introducing hydrogen and the catalyst, preferably the two steps being performed in the same reaction vessel. The general mechanism of reductive aminations is believed to start with the nucleophilic addition of ammonia or a primary or secondary amine species to the carbonyl group of the ketone or aldehyde. Such addition may occur with or without the aid of a catalyst. The resulting adduct, sometimes referred to as "hemiaminal", may react further by the elimination of water to the corresponding imine. The occurrence of imine formation is not essential for the outcome of the reductive amination, and in case of the use of secondary amines as reagents, this even is impossible. In this case, enamines may be formed as intermediates.

The next step in the mechanism of the reductive amination involves a reduction step. All three of an imine, a hemiaminal or an enamine may be the substrate before and on which the reduction is taking place. For this step, a reducing agent is required, which itself will be oxidized after the reaction has been effectuated. Such as for other hydrogenation reactions, stoichiometric reagents are sometimes used for this purpose, such as for instance formic acid or hydrides such as borohydrides or aluminum hydrides, but from the point of view of atom efficiency and process economics, the use of hydrogen gas is particularly favourable.

In an embodiment, the process according to the present invention is for the production of chloroaniline from nitrochlorobenzene using a catalyst other than a bimetallic Pt/Cu on carbon catalyst. Halogenated nitro benzenes are another industrially interesting class of substrates, as they are often used as precursors to produce halogenated anilines which find use in the dye industry and as building blocks in multi-step synthesis protocols of complex active ingredients in the agrochemical or the pharmaceutical industry. The catalyst used in the process according to the present invention may represent an advantageous alternative to the expensive Pt catalysts which are often used in the art. The applicants have found surprisingly that a Pd/Cu catalyst, in spite of the reputation that Pd is supposedly much less selective than Pt, may achieve very high selectivities in also these reactions of high economic importance. The Pd/Cu thus represents an advantageous alternative to the Pt/Cu (10:1 weight ratio) on active carbon powder catalyst proposed for this reaction in U.S. Pat. No. 5,512,529. The applicants believe that this advantage may apply also to a number of other first metals other than Pd, in combination with a number of other second metals other than Cu.

In an embodiment of the process according to the present invention, the heterogeneous catalyst comprises the first metal at a concentration in the range of 0.1-10.0% by weight, preferably at a concentration of at least 0.5% by weight, more preferably at least 1.0%, even more preferably at least 1.5%, yet more preferably at least 2.0%, preferably at least 2.5% by weight, more preferably at least 3.0%, even more preferably at least 3.5%, yet more preferably at least 4.0%, preferably at least 4.5% by weight, and optionally at a concentration of at most 8.0%, preferably at most 7.0%, more preferably at most 6.0% wt, even more preferably at most 5.0% wt, preferably at most 4.0% wt, all based on the total weight of the catalyst. The applicants have found that these levels provide an advantageous balance between catalyst performance and the costs and efforts associated with the production of the catalyst.

In an embodiment of the process according to the present invention, the heterogeneous catalyst comprises the second metal at a concentration in the range of 0.05-40% by weight, preferably at a concentration of at least 0.1% by weight, more preferably at least 0.5%, even more preferably at least 1.0% wt, yet more preferably at least 1.5% wt, preferably at least 2.0% by weight, more preferably at least 3.0% wt, even more preferably at least 4.0% wt, yet more preferably at least 4.5% by weight, preferably at least 5.0% by weight, more preferably at least 5.5% wt, even more preferably at least 6.0% by weight, and optionally at a concentration of at most 35.0% by weight, preferably at most 30.0% wt, more preferably at most 25.0% wt, even more preferably at most 20.0% wt, yet more preferably at most 18.0% wt, preferably at most 16.0% wt, more preferably at most 14.0% wt, even more preferably at most 12.0% wt, yet more preferably at most 10.0% wt, preferably at most 9.5%, more preferably at most 9.0% wt, even more preferably at most 8.5% wt, yet more preferably at most 8.0% wt, preferably at most 7.5% wt, more preferably at most 7.0% wt, even more preferably at most 6.5% wt, all based on the total weight of the catalyst. The applicants have found that these levels of the second metal are also bringing an advantageous compromise between the performance of the catalyst in the process and the complexity and efforts in the production of the catalyst.

In an embodiment, the process according to the present invention further comprises the step of putting the first metal onto a support by precipitation. The applicants have found that the precipitation method is a very convenient method for putting a metal such as palladium onto a support. Suitable precipitation methods for putting palladium metal onto a support are well known in the art.

In an embodiment, the process according to the present invention comprises the step of putting the second metal onto a support by precipitation. This step may be performed at the same time as putting the first metal onto the support, or may be performed after having put the first metal onto the support. The applicants prefer that the second metal is put on the catalyst after having put the first metal onto the support, because they have found that the catalyst prepared as such exhibited an even lower degree of dehalogenation when compared to a catalyst made by co-precipitation.

In an embodiment of the process according to the present invention, the chemical conversion selected from reductive amination and hydrogenation is performed in the presence of a solvent, preferably an organic solvent, preferably the solvent comprising at least one alkanol, preferably methanol, preferably the solvent being present in a weight ratio relative to the organic feed substrate in the range of 0.1-20 g/g, preferably at least 0.2 g/g, more preferably at least 0.3 g/g, optionally at most 15.0 g/g, preferably at most 10.0 g/g, more preferably at most 5.0 g/g, even more preferably at most 4.0 g/g, yet more preferably at most 3.0 g/g, preferably at most 2.0 g/g, even more preferably at most 1.0 g/g. Reductive amination reaction or selective hydrogenations according to the process of the present invention may occur in any suitable medium. Solvents such as water, alcohols (e.g. methanol), tetrahydrofurane (THF), dioxane, alkanes may be used advantageously. A solvent may bring advantages to such reductive amination or hydrogenation reaction, such as an improved hydrogen solubility, a decreased viscosity of the reaction mixture, an improved mixing efficiency, an improved heat transfer, etc. . . . . The concentration of the substrate and products in such solvents may be between 1 and 50%, preferably between 5 and 40%, more preferably between 10 and 40% by weight, based on the total reaction mixture. Highly diluted reaction mixtures may result in poor space-time yields, while in case of highly concentrated reaction mixtures, the benefits of the solvent may be minimized. In case the reaction substrates and products are liquids under the reaction conditions applied, the reaction may be performed without the addition of a solvent. One may also choose to add small amounts of solvents to the reaction mixture, e.g. 1 to 50%, preferably 5 to 40%, more preferably 10 to 30% by weight, relative to the total reaction mixture. Such addition may have particular advantages such as to improve the catalyst performance, to decrease the autogenous pressure of the reaction mixture, to prevent phase separation to occur, etc. . . . .

In case of the reductive amination of o-chloro benzaldehyde with dimethyl amine (DMA), we have found that the addition of small amounts of methanol to the reaction mixture improves the yield and operability of the process significantly. Without wanting to be bound by this theory, the methanol is believed to increase the solubility of the highly volatile amine and therefore enhancing the reaction rate in the liquid phase. Additionally, the presence of methanol may possibly prevent the occurrence of two separate liquid phases during the reductive amination, possible because of any liberation of water as the co-product in the reaction.

In an embodiment of the process according to the present invention, the heterogeneous catalyst has been heat treated, such as prior to its use in the process, preferably at a temperature in the range of 50-500° C., preferably at a temperature of at least 60° C., more preferably at least 70° C., even more preferably at least 80° C., yet more preferably at least 100° C., preferably at least 150° C., more preferably at least 200° C., even more preferably at least 250° C., and optionally at a temperature of at most 450° C., preferably at most 400° C., even more preferably at most 350° C., preferably the heat treatment being performed for at least 2 hours, more preferably 3 hours. The applicants prefer to heat treat the catalyst at about 300° C., in air, for a period of about 3 hours, and this after having dried the catalyst at about 60° C. for a period of 3 hrs, when no substantial further weight loss could anymore be noticed.

The catalyst which is used in the process according to the present invention is preferably a bimetallic catalyst containing Pd and Cu. The metals may occur as a true alloy or as a layered catalyst. In case of a true alloy, no separate Pd or Cu phase may be distinguished anymore. In case of a layered catalyst, a Pd and a Cu phase may occur as alternating in the catalyst on a molecular level. The catalyst according to present invention may also contain a combination of alloyed and pure metal phases. In all cases, it is important that the two metals, Pd and Cu, are in contact with each other and do not exist as separate entities in the reaction mixture or on a support.

In an embodiment of the process according to the present invention, the catalyst comprises Pd and Cu in a weight ratio of Cu relative to Pd in the range of 0.05:1.0 to 10.0:1.0, preferably at least 0.1:1.0, more preferably at least 0.5:1.0, even more preferably at least 1.0:1.0, yet more preferably at least 1.5:1.0, preferably at least 2.0:1.0, and optionally at most 8.0:1.0, preferably at most 6.0:1.0, more preferably at most 5.0:1.0, even more preferably at most 4.0:1.0, yet more preferably at most 3.5:1.0, preferably at most 3.0:1.0, more preferably at most 2.5:1.0. The applicants have found that with the two metals in the ratio's as specified, the activity of the catalyst as well as the desired reaction selectivity to the desired product are improved.

In an embodiment of the process according to the present invention, the heterogeneous catalyst has a support selected from the list consisting of carbon, alumina, silica, zeolite, clay, porous polymer and hybrid polymer, preferably a carbon support, more preferably an activated carbon, even more preferably an activated carbon activated by a treatment with an acid.

For the ease of handling, the catalyst is preferably supported on a solid carrier. A suitable carrier for the support of the metals in the catalyst of the process according to the present invention is activated carbon, because of its large specific surface area and its good adhesion properties. Further treatment, such as steaming, acid washing, sulphonation, or the like, may be given to the support, because this often enhances the adsorption properties of the activated carbon. Other carbon carriers such as graphite or carbon nanotubes (CNB) may be used as the support of the catalyst. Carbon supports offer the additional advantage that the process for recycling the metal or metals, at the end of life of the catalyst, is much simplified as compared with other supports.

Other types of materials known by people skilled in the art may suitably be used as the catalyst support: alumina, silica, zeolite, clay, porous polymer and hybrid polymer, and combinations thereof.

The total metal loading on the catalyst support may be in the range of 0.1 to 40% by weight, more preferably at least 0.2%, more preferably 0.5%, most preferably 1.0%, and optionally at most 35% by weight, preferably at most 30%, more preferably at most 25%, whereby the levels are expressed relative to the total weight of the catalyst.

The supported catalyst may occur in a form which is most suitable and desired for the process, such as a powder, a granule, an extrudates, or combinations thereof. With a powder catalyst, the catalyst may after use be separated from the reaction mixture by filtration. With granules and/or extrudates, the catalyst and the reaction mixture may be separated from each other by simple draining of the reactor vessel containing the catalyst, which may for instance be arranged in a fixed bed arrangement.

In an embodiment of the process according to the present invention, the heterogeneous catalyst has a metal area, as measured by carbon monoxide chemisorption of at least 0.5 $m^2/g$, preferably at least 1.0 $m^2/g$, more preferably at least 2.0 $m^2/g$, even more preferably at least 3.0 $m^2/g$, yet more preferably at least 4.0 $m^2/g$, optionally at most 12.0 $m^2/g$.

In an embodiment of the process according to the present invention, the heterogeneous catalyst has been pre-reduced prior to the step of contacting the catalyst with the organic feed substrate, preferably by subjecting the catalyst at a temperature of at least 120° C., preferably at least 140° C. to a hydrogen atmosphere of at least 5 bar gauge, preferably at least 8 bar gauge during a period of at least 30 minutes, preferably at least 45 minutes, preferably the pre-reduction being performed with the catalyst being in contact with an organic liquid phase, preferably an alkanol, more preferably methanol. The applicants prefer to preform this pre-reduction step with the catalyst in contact with methanol, at a temperature of about 150° C., and under a hydrogen partial pressure of about 10-11 bar absolute, and this for a period of about one hour. The applicants have found that this pre-reduction step allows the catalyst to exhibit its desired advantageous performance from very early on in starting the process.

In an embodiment of the process according to the present invention, at least 80% of the feed substrate is retaining the at least one further functional group after the conversion, preferably at least 85%, more preferably at least 90%, even more preferably at least 95%, preferably at least 97%, more preferably at least 98%, even more preferably at least 99.0%, preferably at least 99.4%, more preferably at least 99.5%, even more preferably at least 99.6% of the feed substrate is retaining the at least one further functional group after the conversion. The applicants have found that these results are readily achievable with the catalyst of the process according to the present invention.

In an embodiment of the process according to the present invention, the chemical conversion selected from reductive amination and hydrogenation is performed at a $H_2$ partial pressure in the range of 0.01-250 bar gauge, preferably at least 0.1, more preferably at least 1, even more preferably at least 5.0 bar gauge, even more preferably at least 10.0 bar gauge, yet more preferably at least 20 bar gauge, preferably at least 30 bar gauge, more preferably at least 40 bar gauge, even more preferably at least 50 bar gauge, and optionally at most 200 bar gauge, preferably at most 150 bar gauge, more preferably at most 100 bar gauge, even more preferably at most 80, yet more preferably 70, and preferably at most 60 bar gauge.

In an embodiment of the process according to the present invention, the chemical conversion selected from reductive amination and hydrogenation is performed at a temperature in the range of 0-300° C., preferably at least 10° C., more preferably at least 20° C., even more preferably at least 30° C., yet more preferably at least 40° C., preferably at least 60° C., more preferably at least 80° C., and even more preferably at least 90° C., and optionally at most 250° C., preferably at most 200° C., more preferably at most 180° C., even more preferably at most 150° C., yet more preferably at most 130° C., preferably at most 120° C., more preferably at most 110° C., even more preferably at most 100° C.

In an embodiment, the process according to the present invention is performed in continuous mode. The applicants have found that the catalyst itself, as well as its performance, may be arranged to be fairly stable over time, such that the process is highly suitable for a continuous operating mode. This brings significant advantages in terms of production rate, volumetric efficiency of the process equipment, control equipment, steadiness of performance, operator attention and intervention frequency, automation capabilities, many of which represent significant advantages to the process owner.

The applicants have found that the process according to the present invention may also be performed in batch mode. The applicants have found that the catalyst, upon separation from the reaction medium after a first performance of the process, may readily be reused in a second performance of the process, preferably without any intermediate treatment. The applicants have found that at least 5, preferably at least 10, and more preferably at least 15 reuse cycles may be performed with the same catalyst in the process according to the present invention. The applicants have found that some metal may leach from the catalyst during the early performances of a fresh catalyst in the process according to the present invention, but that such metal leaching is at a level which is substantially insignificant in terms of amount of metal lost from the catalyst, and also does not cause any substantial loss of performance of the catalyst.

In an embodiment, the process according to the present invention further comprises the purification of the converted substrate, preferably by the distillation of the reaction product, for reducing the content of at least one compound selected from a reaction byproduct, a feed impurity, a solvent, and unreacted feed substrate.

In an embodiment wherein the process according to the present invention is used for the production of ortho-chloro benzyl dimethyl amine, 2-Cl-BDMA, the process is further comprising subjecting the 2-Cl-BDMA to a Grignard reaction, comprising for example in a first step the preparation of a Grignard reagent in which a magnesium atom is introduced in between the benzene ring and the chlorine atom, followed by a second step wherein the Grignard reagent is reacted with an oxalic acid dialkyl ester.

In an embodiment wherein the process according to the present invention is used for the production of ortho-chloro benzyl dimethyl amine, 2-Cl-BDMA, the process is further comprising the conversion of 2-Cl-BDMA into o-chloromethylphenylglyoxylic esters by a method such as described in US 2010/113778 A1. o-Chloromethylphenylglyoxylic esters are important intermediates for preparing agrochemically active compounds or microbicides of the methoximinophenylglyoxylic ester series. More particularly, US 2010/113778 A1 describes the production of strobilurines, a type of fungicides that are stated to inhibit the respiratory system of the fungi, and of which Kresoxim-methyl and Dimoxystrobin are named and exemplified as particularly interesting family members. In a further embodiment therefore, the process according to the present invention further comprises the production of a fungicide composition containing a methoximinophenylglyoxylic ester derivatived from 2-Cl-BDMA, in particular derived from the composition according to the present invention, as well as further comprising the step of using the fungicide composition containing the ester for treating a substrate. The fungicide composition may be solid, such as a powder, or liquid, in which the ester may be dissolved or dispersed. The step of using the fungicide composition may be performed by any one of the methods known in the art, and combinations thereof, such as by spraying, by brushing, by pooring, by dusting, by mixing and the like, including combinations thereof.

In an embodiment of the composition according to the present invention, the composition comprises at least 98.5% wt of 2-chloro-benzyl-dimethylamine, preferably at least 99.0% wt, more preferably at least 99.1% wt, even more preferably at least 99.2% wt, yet more preferably at least 99.3% wt of 2-chloro-benzyl-dimethylamine. The higher the content in 2-chloro-benzyl-dimethylamine, the more advantageously the composition may be applied in its desired application, such as a conversion to a further chemical derivative.

In an embodiment, the composition according to the present invention comprises at most 0.04% wt of 2-chloro-dichloromethyl benzene, preferably at most 0.030% wt, more preferably at most 0.020% wt, even more preferably at most 0.015% wt, preferably at most 0.010% wt, more preferably at most 50 ppm by weight, even more preferably at most 10 ppm, of 2-chloro-dichloromethyl benzene. This component may represent an additional burden in applying the composition, such as generating corrosive components in subsequent reactions, and/or leading to undesired byproducts in subsequent conversions. The lower the content of 2-chloro-benzylchloride, the more advantageously the composition may be applied in its desired application, such as a conversion to a further chemical derivative.

In an embodiment, the composition according to the present invention comprises at least 0.07% wt of 2-chloro-benzyl alcohol, preferably at least 0.09% wt, more preferably at least 0.10% wt, even more preferably at least 0.12% wt, yet more preferably at least 0.15% wt of 2-chloro-benzyl alcohol.

In an embodiment, the composition according to the present invention comprises at most 1.0% wt of 2-chloro-benzyl alcohol, preferably at most 0.80% wt, more preferably at most 0.60% wt, even more preferably at most 0.50% wt, yet more preferably at most 0.40% wt of 2-chloro-benzyl alcohol.

The applicants have found that the 2-chloro-benzyl alcohol may acceptably be present in the composition without jeopardising or affecting the performance of the composition in many of its applications, such as particular conversions into further chemical derivatives, in particular those conversions and uses which have been described in more detail elsewhere in this document. The applicants have found that there is for many of such applications little to no need for the removal of any 2-chloro-benzyl alcohol which may be present in the composition, in particular not when it is present at the levels as specified. This represents an advantage because the removal of 2-chloro-benzyl alcohol from the prime product 2-chloro-benzyl-dimethylamine, and this to very low levels, may bring significant additional complexity to the process.

In an embodiment, the composition according to the present invention comprises at most 0.20% wt of 2-chloro-benzaldehyde, preferably at most 0.15% wt, more preferably at most 0.10% wt, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC, if needed assisted by mass-spectrometry. This 2-chloro-benzaldehyde does not contribute to many of the applications of the composition. A presence at a lower level of this component therefore represents an improved effectiveness and brings improved efficiencies in the further use and application of the composition.

In an embodiment, the composition according to the present invention comprises at most 0.40% wt of 4-chloro-benzyl dimethylamine, preferably at most 0.30% wt, more preferably at most 0.20% wt, even more preferably at most 0.10% wt of 4-chloro-benzyl dimethylamine, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. The applicants have found that this component may represent an additional burden in applying the composition, such as in subsequent reactions, and/or may lead to undesired byproducts in subsequent conversions which in addition may be rather difficult to separate from the desired product of such conversion. The lower the content of 4-chloro-benzyl dimethylamine, the more advantageously the composition may be applied in its desired application, such as a conversion to a further chemical derivative.

In an embodiment, the composition according to the present invention comprises at most 0.35% wt of ortho-chloro toluene, preferably at most 0.30% wt, more preferably at most 0.20% wt, even more preferably at most 0.10% wt of ortho-chloro toluene, preferably at most 0.05% wt, more preferably at most 0.03% wt, even more preferably at most 0.01% wt, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. Preferably the specified levels apply to the total of all chloro toluene isomers together. The applicants have found that this component, and also its isomers, may represent an additional burden in applying the composition, such as in subsequent reactions, and/or may lead to undesired byproducts in subsequent conversions which in addition may be rather difficult to separate from the desired product of such conversion. The lower the content of chloro toluenes, in particular of ortho-chloro toluene, the more advantageously the composition may be applied in its desired application, such as a conversion to a further chemical derivative.

In an embodiment, the composition according to the present invention comprises at most 0.40% wt of benzyl dimethyl amine, preferably at most 0.30% wt, more preferably at most 0.20% wt, even more preferably at most 0.10% wt of benzyl dimethyl amine, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. This benzyl dimethyl amine does not contribute to many of the applications of the composition. A presence at a lower level of this component therefore represents an improved effectiveness and brings improved efficiencies in the further use and application of the composition.

In an embodiment, the composition according to the present invention comprises at most 0.40% wt of 2-dimethylaminobenzyl dimethylamine, preferably at most 0.30% wt, more preferably at most 0.20% wt, even more preferably at most 0.10% wt of 2-dimethylaminobenzyl dimethylamine, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. This 2-dimethylamino-benzyldimethylamine does not contribute to many of the applications of the composition. A presence at a lower level of this component therefore represents an improved effectiveness and brings improved efficiencies in the further use and application of the composition.

In an embodiment, the composition according to the present invention comprises at most 0.40% wt of benzaldehyde, preferably at most 0.30% wt, more preferably at most 0.20% wt, even more preferably at most 0.10% wt of benzaldehyde, preferably at most 0.05% wt, more preferably at most 0.020% wt, even more preferably at most 0.010% wt, preferably at most 50 ppm by weight, more preferably at most 10 ppm, even more preferably at most 5 ppm, yet more preferably at most 1 ppm by weight, as determined by gas chromatography, GC. This benzaldehyde does not contribute to many of the applications of the composition. A presence at a lower level of this component therefore represents an improved effectiveness and brings improved efficiencies in the further use and application of the composition.

In an embodiment, the composition according to the present invention is produced by the process according to the present invention. The applicants have found that the process according to the present invention is particularly suitable for producing the composition, because the process is able to provide a high reaction rate and conversion to the desired 2-chloro-benzyl-dimethylamine, which achieves low levels of the unconverted feed substrate 2-chloro-benzaldehyde, and thanks to the high selectivity of the catalyst as specified, with low presence of less desired byproducts, such as 2-chloro-benzyl alcohol and/or benzyl dimethyl amine and/or 2-dimethylamino-benzyldimethylamine. In addition, the process according to the present invention for the production of 2-chloro-benzyl-dimethylamine has little to no presence of the other undesired components 2-chloro-benzylchloride and/or 4-chloro-dimethylbenzylamine and/or chloro toluene isomers, in particular ortho-chloro toluene. The composition according to the present invention as obtainable by the process according to the present invention is thus particularly suitable for use in many of its applications, such as particular conversions into further chemical derivatives, in particular those conversions and uses which have been described in more detail elsewhere in this document.

Analyticals

For analysing the composition according to the present invention, as well as in the monitoring of the process according to the present invention, the applicants prefer to use the following gas chromatography, GC, analytical method.

The GC apparatus is preferably an Agilent 6890N with split injector and a flame ionization detector (FID). The apparatus is equipped with a capillary column coated with a stationary phase type CP-Sil 5 CB with dimensions 60 m×320 µm×5.0 µm. The applicants prefer to use an injector temperature of 280° C., an injector volume of 1 µliter and a split ratio of 1/30. The applicants prefer to use helium as the carrier gas, with a flow of 2 ml/min at constant flow. The oven is given a temperature program of holding for 3 minutes at 60° C., and subsequently ramping up the temperature at a rate of 20° C. per minute up to 290° C., at which temperature the column is kept for an additional 15 minutes. The FID detector is kept at 300° C., and fed with a hydrogen flow of 45 ml/min and an air flow of 450 ml/min. Make up gas, preferably nitrogen, and column flow together are set at a total of 45 ml/min.

The applicants have found that the following components may readily be identified by specific retention peaks: methanol, DMA, TMA, ethylbenzene, benzaldehyde, benzyl dimethyl amine, ortho-chloro benzaldehyde, ortho-chloro benzylalcohol, ortho-chloro benzyl dimethyl amine, para-chloro benzyl dimethyl amine, ortho (dimethylamino) benzyl dimethyl amine. The applicants have further found that this GC technique may readily be assisted with the addition of mass-spectrometry, such as for determining concentrations in the lower levels down to 1 ppm wt or even below.

Depending on the sample, the sample may be diluted up to 10 times in isopropanol. Preferably 1% of the internal standard is added, upon which the sample is preferably vigorously mixed for at least one minute, and after which 1 µl of sample may be injected into the gas chromatograph.

EXAMPLES

Where percentages are given in these examples, they mean percentages in weight, unless otherwise specified.

Example 1: Preparation and Activation of the Pd/Cu Catalyst 10 g of a 5% wt palladium on carbon catalyst, as this is commercially available under the reference E196NN/W from the company Evonik, was stirred in 300 mL of an aqueous solution of copper nitrate (6.7 g/L). 50 ml of an aqueous solution of sodium carbonate (38.4 g/L) were added slowly under vigorous stirring at room temperature over a period of 3 minutes. This solution was then stirred for another 15 minutes at room temperature and 15 minutes at a temperature of 75° C. The catalyst was then filtered off and dried in an oven at the temperature of 60° C. until complete dryness. After that, the catalyst was calcined in air at 300° C. for 3 hours and reduced in methanol at a temperature of 150° C. and under a hydrogen partial pressure of 10 bar. Afterwards, the catalyst was filtered off until a paste was obtained. This paste was containing 5.67% of palladium and 13.7% of copper.

Example 2: Reductive Amination of 2-Chloro-Benzaldehyde with DMA to Produce 2-Cl-BDMA A 300 mL autoclave (Parr) was loaded with 90 g of 2-chloro benzaldehyde (Sigma Aldrich) and 54 g of methanol (industrial grade). The reactor was sealed and the gas phase was flushed three times with nitrogen. Then, 40 g of dimethyl amine was added to the reaction mixture, causing the temperature to increase to 55° C. in 5 minutes time. The reactor was further heated in 10 minutes to the desired temperature of 80° C. The reactor pressure was set to 10 bar by the addition of nitrogen gas. Stirring was then continued for 60 minutes at a temperature of 80° C. and a pressure of 10 bar. Then, the reactor was cooled to 30° C. and degassed. 0.1 g of the catalyst from example 1 was added to the autoclave. The autoclave was heated in 15 minutes to 90° C. and hydrogen was added to a final pressure of 55 bar. The hydrogenation reaction was allowed to proceed for 5 h at 90° C. Then the reactor was cooled down and degassed at room temperature. A sample was taken and analyzed by GC and ICP The catalyst was then filtered and re-used again in a repeat experiment using the same conditions, in a second run.

The tables below report the results obtained, all expressed in weight units relative to the total weight of the reaction product disregarding water, methanol and any residual dimethylamine that might still be present.

Product of the First Reaction:

| 2-Cl-BZA (%) | BDMA (%) | 2-Cl-BDMA (%) | DMA-BDMA (%) | 2-Cl-BOH (%) | Others (%) | Pd (ppm) | Cu (ppm) |
|---|---|---|---|---|---|---|---|
| Nd | 0.04 | 99.14 | 0.16 | 0.47 | 0.19 | <0.5 | 7.42 |

Product of the Second Run:

| 2-Cl-BZA (%) | BDMA (%) | 2-Chloro-BDMA (%) | DMA-BDMA (%) | 2-Chloro-benzylOH (%) | Others (%) | Pd (ppm) | Cu (ppm) |
|---|---|---|---|---|---|---|---|
| 0.03 | 0.08 | 98.82 | 0.17 | 0.73 | 0.17 | <0.5 | 1.56 |

Legend:
Nd Not detected
2-Cl-BZA 2-chloro-benzaldehyde
BDMA Benzyl dimethylamine
2-Cl-BDMA 2-chlorobenzyl dimethylamine
DMA-BDMA 2-dimethylaminobenzyl dimethylamine
2-Cl—BOH 2-chlorobenzyl alcohol It is observed that the selectivities and yields remained substantially the same for both runs, and that they were exceptionally high in favour of the desired product 2Cl-BDMA. It may be further observed that some leaching of Cu metal occurred in the first run, but that this was strongly reduced already during the second run.

Example 3: Reductive Amination of Ortho-Chloro-Benzaldehyde with DMA

Methanol (27 g), ortho-chloro-benzaldehyde (2-Cl-BZA, 90 g) and dimethylamine (DMA, 37 g) were introduced into a 300 ml high pressure reactor. Dimethylamine was introduced by connecting the autoclave with a bomb containing liquid DMA. Nitrogen was fed into the reactor until a pressure of 10 barg was reached. The mixture was heated to 80° C. and was kept at this temperature under constant stirring (450 rpm) for 1 hour. The mixture was cooled to room temperature and the reactor was vented. The catalyst, containing 3% wt Pd and 7% wt Cu on carbon, was prepared by slurrying a 3% wt Pd/C catalyst in demineralised water. Then, an appropriate amount of $CuCl_2$ aqueous solution was added to the slurry. Subsequently, aqueous $NaHCO_3$ was added until the pH reached 7-7.2. The resulting slurry was then heated, and a chemical reduction was performed by means of adding sodium formate. During this procedure, gas was released from the slurry and the temperature was further increased to 95° C. Then, the slurry was cooled, decanted or filtered, and washed with fresh demineralised water. Prior to use in the experiment the catalyst was reduced at 180° C. under hydrogen at 10 barg hydrogen for 1 hour.

This catalyst was introduced into the cooled and vented reaction mixture and hydrogen was fed into the reactor until a pressure of 70 barg was reached. The mixture was heated to 100° C. and was kept at this temperature under constant stirring (900 rpm) for 1 hour. The exact same procedure was performed with a 5% Pd on carbon catalyst which had not been pre-reduced.

The results are reported in the following table:

| | | Selectivity (%) | | | |
|---|---|---|---|---|---|
| Catalyst | Conversion (%) | 2Cl-BDMA | BDMA | 2-Cl-BOH | BOH | Others |
| Pd on C | 99.9 | 33.4 | 45.8 | 0.16 | <0.05 | 20.6 |
| Pd/Cu on carbon | 99.9 | 98.25 | 0.46 | 0.37 | <0.05 | 0.86 |

Legend (further to the symbols defined herein above):
BOH Benzyl alcohol

Example 4: Reductive Amination of 4-chloro-benzaldehyde to 4-chloro-benzyl dimethylamine Methanol (27 g), para-chloro-benzaldehyde (4-Cl-BZA, 90 g) and dimethylamine (DMA, 37 g) were introduced into a 300 ml high pressure reactor. Dimethylamine was introduced by connecting the autoclave with a bomb containing liquid DMA. Nitrogen was fed into the reactor until a pressure of 10 barg was reached. The mixture was heated to 80° C. and was kept at this temperature under constant stirring (450 rpm) for 1 hour. The mixture was cooled to room temperature and the reactor was vented. The catalyst, containing 3% wt Pd and 7% wt Cu on carbon, and which was reduced prior to the experiment at 180° C. under hydrogen at 10 barg for 1 hour, was introduced into the reaction mixture and hydrogen was fed into the reactor until a pressure of 70 barg was reached. The mixture was heated to 100° C. and was kept at this temperature under constant stirring (900 rpm) for 1 hour. The exact same procedure was performed with a 5% Pd on carbon catalyst, which was not pre-reduced.

The results are reported in the following table:

| | | Selectivity (%) | | |
|---|---|---|---|---|
| Catalyst | Conversion (%) | 4-Cl-BDMA | BDMA | Others |
| Pd/C | 83.1 | 30.2 | 48.3 | 20.6 |
| Pd/Cu on C | 75 | 96.4 | 1.9 | 0.86 |

Legend (further to the symbols defined herein above):
4-Cl-BDMA 4-chlorobenzyl dimethylamine

Example 5: Reductive Amination of 2,4-dichloro-benzaldehyde to 2,4-dichlorobenzyl dimethylamine Methanol (27 g), 2,4-dichloro-benzaldehyde (2,4-Cl-BZA, 90 g) and dimethylamine (DMA, 30 g) were introduced into a 300 ml high pressure reactor. Dimethylamine was introduced by connecting the autoclave with a bomb containing liquid DMA. Nitrogen was fed into the reactor until a pressure of 10 barg was reached. The mixture was heated to 80° C. and was kept at this temperature under constant stirring (450 rpm) for 1 hour. The mixture was cooled to room temperature and the reactor was vented. The catalyst, containing 3% wt Pd and 7% wt Cu on carbon, which was reduced prior to the experiment at 180° C. under hydrogen at 10 barg for 1 hour, was introduced into the reaction mixture and hydrogen was fed into the reactor until a pressure of 70 barg was reached. The mixture was heated to 100° C. and was kept at this temperature under constant stirring (900 rpm) for 15 minutes. The exact same procedure was performed with a 5% Pd on carbon catalyst, which was not pre-reduced.

The results are reported in the following table:

| Catalyst | Conversion (%) | Selectivity (%) | | |
|---|---|---|---|---|
| | | 2,4-Cl-BDMA | BDMA | Others |
| Pd/C | 78.3 | 30.5 | 48.2 | 21.3 |
| Pd/Cu on C | 68.3 | 96.8 | 1.9 | 1.2 |

Legend (further to the symbols defined herein above):
2,4-Cl-BDMA 2,4-chlorobenzyl dimethylamine

Example 6: Hydrogenation or 2-Chloro-benzaldehyde to 2-Chloro-benzyl Alcohol Water (150 g), ortho-chloro-benzaldehyde (2-Cl-BZA, 30 g) were introduced into a 300 ml high pressure reactor, together with the catalyst containing 3% wt Pd and 7% wt Cu on carbon (0.11 g). Hydrogen was fed into the reactor until a pressure of 20 barg was reached. The mixture was heated to 100° C. and was kept at this temperature under constant stirring (900 rpm) for 2 hours. The exact same procedure was performed with a 5% Pd on carbon catalyst, which was not pre-reduced.

The results are reported in the following table:

| Catalyst | Conversion (%) | Selectivity (%) | | | | |
|---|---|---|---|---|---|---|
| | | 2-Cl-BOH | BOH | Toluene | BZA | Others |
| Pd on C | 40.25 | 12.50 | 35.39 | 0.70 | 16.87 | 34.54 |
| Pd/Cu on C | 37.5 | 58.74 | 15.61 | 11.96 | 4.87 | 8.82 |

Legend (further to the symbols defined herein above):
2-Cl-BOH 2-chloro-benzyl alcohol
BZA Benzaldehyde

Example 7: Hydrogenation or 2-Chloro-nitrobenzene to 2-Chloro-aniline

Ethanol (150 g), ortho-chloro-nitrobenzene (30 g) were introduced into a 300 ml high pressure reactor, together with the catalyst containing 3% wt Pd and 7% wt Cu on carbon (0.11 g). Hydrogen was fed into the reactor until a pressure of 20 barg was reached. The mixture was heated to 50° C. or to 100° C. and was kept at this temperature under constant stirring (900 rpm) for 2 hours. The exact same procedure was performed with a 5% Pd on carbon catalyst, which was not pre-reduced.

The results are reported in the following table:

| Catalyst | Temperature | Conversion (%) | Selectivity (%) | |
|---|---|---|---|---|
| | | | 2-Cl-aniline | Aniline |
| Pd on C | 50° C. | 97.3 | 66 | 34 |
| Pd/Cu on C | 50° C. | 11.1 | 100 | 0 |
| Pd/Cu on C | 100° C. | 97.7 | 93 | 7 |

Example 8: Reductive Amination of 4-bromo-benzaldehyde to 4-bromo-benzyl dimethylamine Methanol (27 g), para-bromo-benzaldehyde (4-Br-BZA, 90 g) and dimethylamine (DMA, 27 g) were introduced into a 300 ml high pressure reactor. Dimethylamine was introduced by connecting the autoclave with a bomb containing liquid DMA. Nitrogen was fed into the reactor until a pressure of 10 barg was reached. The mixture was heated to 80° C. and was kept at this temperature under constant stirring (450 rpm) for 1 hour. The mixture was cooled to room temperature and the reactor was vented. The catalyst, containing 3% wt Pd and 7% wt Cu on carbon, which was reduced prior to the experiment at 180° C. under hydrogen at 10 barg for 1 hour, was introduced into the reaction mixture and hydrogen was fed into the reactor until a pressure of 70 barg was reached. The mixture was heated to 100° C. and was kept at this temperature under constant stirring (900 rpm) for 1 hour. The exact same procedure was performed with a 5% Pd on carbon catalyst, which was not pre-reduced.

The results are reported in the following table:

| Catalyst | Conversion (%) | Selectivity (%) | | |
|---|---|---|---|---|
| | | 4-Br-BDMA | BDMA | Others |
| Pd/C | 99.8 | 0.4 | 88.0 | 11.6 |
| Pd/Cu on C | 99.72 | 80.7 | 16.0 | 3.3 |

Legend (further to the symbols defined herein above):
4-Br-BDMA 4-bromo-benzyl dimethylamine

Example 9: Reductive Amination of 2-bromo-benzaldehyde to 2-bromo-benzyl dimethylamine Methanol (27 g), ortho-bromo-benzaldehyde (2-Br-BZA, 90 g) and dimethylamine (DMA, 37 g) were introduced into a 300 ml high pressure reactor. Dimethylamine was introduced by connecting the autoclave with a bomb containing liquid DMA. Nitrogen was fed into the reactor until a pressure of 10 barg was reached. The mixture was heated to 80° C. and was kept at this temperature under constant stirring (450 rpm) for 1 hour. The mixture was cooled to room temperature and the reactor was vented. The catalyst, containing 3% wt Pd and 7% wt Cu on carbon, which was reduced prior to the experiment at 180° C. under hydrogen at 10 barg for 1 hour, was introduced into the reaction mixture and hydrogen was fed into the reactor until a pressure of 70 barg was reached. The mixture was heated to 100° C. and was kept at this temperature under constant stirring (900 rpm) for 15 minutes. The exact same procedure was performed with a 5% Pd on carbon catalyst, which was not pre-reduced.

The results are reported in the following table:

| Catalyst | Conversion (%) | Selectivity (%) | | |
|---|---|---|---|---|
| | | 2-Br-BDMA | BDMA | Others |
| Pd/C | 74.8 | 25.5 | 58.3 | 16.2 |
| Pd/Cu on C | 73.2 | 81.3 | 8.4 | 10.3 |

Legend (further to the symbols defined herein above):
2-Br-BDMA 2-bromo-benzyl dimethylamine

Example 10: Comparison of Catalysts for the Reductive Amination of 2-chloro-benzaldehyde with DMA to Produce 2-Cl-BDMA Amination Step:

2-Chloro-benzaldehyde (2-Cl-BZA) and methanol (0.3 g/g 2-Cl-BZA) were added to a 100 ml high pressure reactor. The reactor was closed and dimethylamine (DMA) (1.3 equivalents based on 2-Cl-BZA) was added using a solution of DMA in methanol (2M). The mixture was stirred (1500 rpm with hollow shaft stirrer) at 75° C. under 10 barg of nitrogen for 1 hour. Then the reactor was cooled down and the pressure released.

Hydrogenolysis Step:

The selected catalyst (3 mg total weight of catalyst per gram of 2-Cl-BZA) was added to the reaction mixture of the amination step. The reactor is purged three times with nitrogen and then the reactor was put under hydrogen pressure of 70 barg. The reaction mixture was stirred (1500 rpm with a hollow shaft stirrer) and heated up to 100° C. After 15 minutes the reactor was cooled down and flushed with nitrogen. The catalyst was filtered off and the sample was analysed by gas chromatography (GC).

In this example, a monometallic Pd-on-C catalyst was compared with a bimetallic Pd/Cu on C catalyst, first as such and a second time after having been heat treated prior to its use in the example.

The results are reported in the following table:

| Catalyst | Conversion (%) after 15 minutes | Selectivity (%) | | | | |
|---|---|---|---|---|---|---|
| | | BDMA | 2Cl-BDMA | 2-Cl-BDMA | 2-Cl-BOH | Others |
| 5% Pd on C | 99.9 | 45.8 | 33.4 | Nd | 0.15 | 20.65 |
| 3% Pd—7% Cu on carbon | 98.3 | 1.5 | 96.2 | Nd | 2.1 | Nd |
| 3% Pd—7% Cu on carbon, calcined under N2 (*) | 97.6 | 0.2 | 99.3 | Nd | 0.1 | Nd |

(*) The calcination or heat treatment comprised a calcination in a tubular furnace in nitrogen flow (30 ml/min) at 400° C. for 2 hours.

The symbols in this table are the same as in Examples 2 and 3 above.

The 3% Pd-7% Cu on carbon was produced as described in Example 3.

The monometallic 5% Pd on carbon catalyst was obtained as a commercial catalyst offered by the company Evonik, as in all the examples.

The analytical techniques used in this example had a higher detection limit compared to the preceding examples. This explains why certain components which could be found in the preceding examples, stayed below the detection limit in this example.

Example 11: Investigation of Different Bimetallic Systems

The same reaction was performed as in Example 10, following exactly the same experimental protocol but with different kind of catalysts, in particular Pd/Au, Pd/Ni, Pd/Ag, and Pd/Fe.

The catalysts were prepare by impregnating the monometallic Pd catalyst from Example 10 respectively with $NaAuCl_4$, $Ni(NO_3)_2 \cdot 6H_2O$, $AgNO_3$, and $Fe(NO_3)_3 \cdot 9H_2O$. In more detail: 0.5 g of the monometallic Pd catalyst was dispersed in 50 ml of distilled water. A metal precursor solution containing $5 \times 10^{-2}$ molar of the selected second metal (M) precursor compound was added to the dispersion under vigorous stirring. The catalyst was filtered and washed several times with water. The material obtained was then suspended in distilled water and a freshly prepared solution of NaBH4 (0.1 molar) was added under vigorous stirring at room temperature. The sample was filtered, washed and dried at 80° C. for 4 hours. In all the cases the ratio of Pd/M was 1:2 wt/wt and the quantitative adsorption was checked by Atomic Adsorption.

The results are reported in the following table:

| Catalyst (all on carbon support) | Conversion (%) after 15 minutes | Selectivity (%) | | | | |
|---|---|---|---|---|---|---|
| | | BDMA | 2Cl-BDMA | 2-Cl-BDMA | 2-Cl-BOH | Others |
| 3% Pd—7% Cu | 98.3 | 1.5 | 96.2 | Nd | 2.1 | Nd |
| 5% Pd—10% Au | 95.6 | 2.9 | 96.2 | 0.8 | Nd | Nd |
| 5% Pd—10% Ni | 80.6 | 1.0 | 97.9 | Nd | 1.0 | Nd |
| 5% Pd—10% Ag | 72.2 | Nd | 98.9 | Nd | 1.0 | Nd |

All the bimetallic catalysts showed good activity and good selectivity to 2-Cl-BDMA. In particular the Pd/Ag catalyst showed a higher selectivity that the catalyst having 3% Pd and 7% Cu.

Example 12: Reductive Amination of Benzaldehyde with 2-Cl-aniline

The experimental protocol was identical to this of Example 10, except that different starting materials were used, and as catalysts were used the commercial monometallic 5% Pd-on-C catalyst and the 3% Pd-7% Cu on carbon catalyst which was used in several of the preceding examples.

The results are reported in the following table:

| Catalyst | Conversion (%) | Selectivity (%) | | |
|---|---|---|---|---|
| | | N-B, 2-Cl-aniline | N-B aniline | Others |
| Pd/C | 68 | 27.3 | 66.5 | 6.2 |
| Pd/Cu on C | 22 | 58.3 | 33.5 | 8.2 |

Legend (further to the symbols defined herein above):
N-B, 2-Cl-aniline N-benzyl, 2-Chloro-aniline
N-B aniline N-benzyl aniline

Having now fully described this invention, it will be appreciated by those skilled in the art that the invention can be performed within a wide range of parameters within what is claimed, without departing from the scope of the invention, as defined by the claims.

The invention claimed is:

1. A composition comprising, as measured by gas chromatography, GC,
    a) at least 98.0% wt of 2-chloro-benzyl-dimethylamine,
    b) at most 0.40% wt of ortho-chloro toluene, and
    c) at least 0.05% wt of 2-chloro-benzyl alcohol,
    and wherein the composition is prepared from the reductive amination of ortho-chloro benzaldehyde, and wherein the weights of water, solvent and any residual dimethyl amine are excluded from the composition.

2. The composition according to claim 1, comprising at least 98.5% wt of 2-chloro-benzyl-dimethylamine.

3. The composition according to claim 1, further comprising not more than 0.04% wt of 2-chloro dichloromethyl benzene.

4. The composition according to claim 1 comprising at least 0.07% wt of 2-chloro-benzyl alcohol.

5. The composition according to claim 1 comprising not more than 1.0% wt of 2-chloro-benzyl alcohol.

6. The composition according to claim 1 comprising no more than 0.20% wt of 2-chloro-benzaldehyde, as determined by gas chromatography, GC.

7. The composition according to claim 1, further comprising no more than 0.40% wt of 4-chloro-benzyl dimethylamine, as determined by gas chromatography, GC.

8. The composition according to claim 1 comprising no more than 0.35% wt of ortho-chloro toluene.

9. The composition according to claim 1, further comprising not more than 0.40% wt of benzyldimethylamine, as determined by gas chromatography, GC.

10. The composition according to claim 1, further comprising not more than 0.40% wt of 2-dimethylamino-benzyldimethylamine, as determined by gas chromatography, GC.

11. The composition according to claim 1, further comprising not more than 0.40% wt of benzaldehyde, as determined by gas chromatography, GC.

* * * * *